(12) United States Patent
Nielsen

(10) Patent No.: US 6,627,620 B1
(45) Date of Patent: Sep. 30, 2003

(54) COMPOSITION SET AND KIT FOR USE IN INTRAOCULAR SURGERY

(76) Inventor: Per Julius Nielsen, Mirabellevej 12, DK-8240 Risskov (DK)

( * ) Notice: Subject to any disclaimer, the term of this patent is extended or adjusted under 35 U.S.C. 154(b) by 0 days.

(21) Appl. No.: 09/868,136

(22) PCT Filed: Dec. 13, 1999

(86) PCT No.: PCT/DK99/00695

§ 371 (c)(1),
(2), (4) Date: Jun. 29, 2001

(87) PCT Pub. No.: WO00/37047

PCT Pub. Date: Jun. 29, 2000

(30) Foreign Application Priority Data

Dec. 18, 1998 (DK) .......................... 1998 01679

(51) Int. Cl.[7] ............................................. A61K 31/715
(52) U.S. Cl. ........................ 514/54; 514/912; 424/78.04
(58) Field of Search ................. 514/54, 912; 424/78.04

(56) References Cited

U.S. PATENT DOCUMENTS

| 5,143,731 A | 9/1992 | Viegas et al. |
| 5,599,534 A | 2/1997 | Himmelstein et al. |
| 5,612,027 A | 3/1997 | Galin et al. |

FOREIGN PATENT DOCUMENTS

| DK | 171029 | 4/1996 |
| EP | 0138572 | 7/1990 |
| EP | 0517160 | 12/1992 |
| EP | 1097718 | 12/1993 |
| EP | 0535200 | 11/1999 |
| WO | 9841171 | 9/1998 |

OTHER PUBLICATIONS

FASS 1998, Linfo, Läkemdelsinformation AB, Stockholm, pp. 578–579, 1265.

*Primary Examiner*—Zohreh Fay
(74) *Attorney, Agent, or Firm*—Dykema Gossett PLLC

(57) ABSTRACT

A new composition set and a kit for use by intraocular operations, preferably cataract operations. The composition set comprises a first and a second viscoelastic agent, e.g. sodium hyaluronate, containing an anaesthetic, e.g. lidocaine hydrochloride. Hereby a simplified operation and anaesthesia is achieved while at the same time the risk of complications and discomfort on the patient are reduced.

13 Claims, No Drawings

COMPOSITION SET AND KIT FOR USE IN INTRAOCULAR SURGERY

BACKGROUND OF THE INVENTION

The present invention relates to a composition set and a kit for use in intraocular surgery, preferably in cataract operations.

The present invention has appeared in connection with intraocular operations, especially operations for cataract.

In the following the problems will primarily be described in connection with such surgical interventions, however it will be within the scope of the invention to indicate composition set and kit which may be used in connection with other kinds of intraocular operations.

In connection with operating the eye for cataract, a marked change with the technique used by local anesthesia has occurred within the recent years. This has taken place with the intention of introducing less risky techniques.

In recent years, traditional injection behind the eyeball has been substituted by drops with local anaesthetic effect on the surface of the eye. Pain and discomfort may arise in connection with an operation anaesthesia with drops. This is probably caused by movements and pulling, especially of iris. Patients only having been anaesthetised in the surface of the eye have described greater or lesser feeling of discomfort and pain during the operation. These drawbacks have, however, not diminished the popularity of anaesthesia with drops. The patients have thus found it advantageous to avoid the injection behind the eyeball and also for the surgeons drop anaesthesia is a rational advantage.

It has appeared that the discomfort experienced by the patient, only to a small degree is influenced by sedatives given pre- or peri-operatively. On the contrary, it has appeared that the discomfort may be reduced by intraocular use of local anaesthesia.

Therefore, in the later years is has been practice to combine the anaesthesia with drops with intraocular local anaesthesia, preferably lidocaine hydrochloride in a concentration of 1%, which is injected into the anterior eye chamber at the beginning of the operation and later, possibly before implantation of an artificial lens in the eye.

Seeing that the present invention especially will be used in connection with operations for cataract, a more detailed description of such a surgical technique will be given.

The larger part of all surgical interventions takes place in local anaesthesia where, before the operation, sedatives are given and dilatation of the pupil is established. In situations where injection or infiltration anaesthesia is used, injections are given between 10 and 20 minutes before an operation. This is usually given by the surgeon or anaesthetist. By anaesthesia with drops, only drops with local anaesthetic effect are given from about 15 minutes before the start of the operation. This is given by operating theatre assistants. Normally the application of drops is repeated 3–6 times before the operation and it may possibly be supplemented during the operation.

By anaesthesia with drops, the drops are given by nurses, and the surgeon may initiate the operation immediately when preparation in the form of washing and exposing has been performed by a nurse.

The surgeon initiates the intervention by making a small incision in the eye at the rim of the cornea. Herethrough intraocular anaesthesia is given by injection of about 0.2 ml in the anterior eye chamber at first. Thereafter the viscoelastic agent is injected as an amount of about 0.2 ml in the anterior eye chamber. This is to prevent collapsing of the eye as well as giving protection to the back of the cornea during the operation.

Hereafter an opening is established at a second position along the rim of the cornea, the opening serving as access for the operation itself. Through this second opening a hole is made in the lens capsule (capsulorhexis), after which the lens is released in the capsule by means of liquid. Then the core and the cortex of the lens are removed with so-called Phaco emulsification and suction. This implies that the lens is split up into smaller pieces that may be sucked out. The remaining capsule now appears as a sack suspended with thin threads (zonula threads). This sack is used as fixation of the new artificial lens in the posterior chamber of the eye right behind the pupil.

Immediately before implantation of the artificial lens, the sack is filled with viscoelastic agent. At the same time, the intraocular anaesthetic may possibly be supplemented before implantation of the lens. After implantation of the lens, the viscoelastic agent is sucked out of the eye. The tightness of the wound is ensured, possibly by means of a suture, and hereafter the operation is finished.

In cases where anaesthesia with drops is used, possibly combined with intraocular anaesthesia, the patient is able to see immediately after the operation has been finished and it is not necessary to make a dressing. This is an advantage as compared to the earlier known injection anaesthesia where is was necessary to provide the patient with a dressing and where the patient had to wait one day before he was able to see.

By the more recent techniques used for operation of cataract today, viscoelastic agents are used by routine, the agents comprising methyl hydroxypropyl cellulose, sodium hyaluronate, or sodium chondroitin sulphate, or mixtures thereof. The viscoelastic agents may be of different molecular weight and concentration and thereby different viscosity.

By the cataract surgery introduced in the later years, viscoelastics have achieved wide speed application. It has been possible to acquire such a viscoelastic as a commercial product for use in eye surgery. Thus it is possible to acquire the agent provided in syringes ready for use at the operation. Viscoelastics were initially prescription drugs but today they have status as over-the-counter drugs for use in intraocular surgery.

The local anaesthesia necessary for cataract operations is sufficient as anaesthesia with drops only. By the newer forms of cataract surgery (Phaco emulsification of the core of the lens through small incisions) it has only been necessary to achieve pain relief at the surface of the eye (analgesia), where it has not been necessary to establish a condition where the eye is standing still (akinesia) or a situation where the eye cannot see (amaurosis). In order to establish analgesia, an anaesthesia with drops has been applied, with dripping from 3 to 6 times as from 15 minutes before the operation until possibly during the operation. This has appeared to be sufficient in order to perform the surgical intervention in a secure and rational way. As previously mentioned, some patients have experienced discomfort when only anaesthesia with drops has been used, probably provoked by structures within the eye. This discomfort has caused increased use of pre- as well as peri-operative sedation by cataract surgery in anaesthesia with drops with the consequent risks of potential complications provoked by this sedation. Also, the discomfort of the patient during anaesthesia with drops has given rise to tensions and uneasiness with disadvantageous consequences for the surgeon's working conditions.

The intraocular anaesthesia used for relieving this discomfort is a specially made product not made or known commercially. It will thus be necessary to suck up anaesthesics into syringes which are transferred to the sterile preparation. There is a possibility of variation in the quality (purity and concentration) of the product made and an irrationality at the individual making of this anaesthesic. Furthermore, by the handling there is a not insignificant risk of contamination and maybe exchange by mistake as other syringes are also used at the operation.

The quality of the product made is critical. Thus the concentration is especially critical as experience shows that higher concentrations probably are toxic to the cornea. Furthermore, anaesthesia of the retina has been described.

In practice only small amounts between 0.2 and 0.5 ml are used, which are injected in one or more doses during the operation. Usually there is used between 0.2 and 0.3 ml at the start of the operation corresponding to the need for viscoelastic agent which is used simultaneously for expanding the anterior eye section at the beginning of the operation. Later there is possibly used an amount of about 0.2 ml before the implantation of the lens, which also mainly corresponds to the need for viscoelastic substance at the lens implantation. Viscoelastic agent and intraocular anaesthesia are thus used in identical amount and at the same time during the operation. They are both applied on the same spot—namely: The anterior eye section.

Intrtocular anaesthesia is used because pressure changes occur in the eye during the operation, especially because of suction of the lens substance, or because manipulation may cause pull on iris, whereby the iris plate may move up and down, this being experienced as discomfort for the patient The intraocular anaesthesia is thus used for removing discomfort for the patient provoked from the inner structure of the eye, so that the patient lies still even at oscillations in pressure by suction and by draught on iris, for example during implantation of the lens. The intraocular anaesthesia makes it possible to perform a more efficient eye operation. Thus it will be possible for more surgeons to muter cataract operations with anaesthesia with drops in addition to that more patients may tolerate anaesthesia with drops. However, in many cases the intraocular anaesthesia is done without bemuse of the risks connected with the procedure and the trouble connected with providing and making suitable mixtures of the used anaesthetics.

For many years, surgery within the eye and especially surgery of cataract has been influence by the desire of still increasing efficiency.

It is an object of the present invention to provide a composition set and a kit making it possible to avoid the drawbacks by the known anaesthetic techniques with anaesthesia with drops, and which at the same time maintains the possibility of ensuring quietness during the operation and which makes it possible to relieve the discomfort on the patient and at the same time makes the surgical intervention more efficient.

SUMMARY OF THE INVENTION

According to the present invention this is achieved by a composition set of the kind mentioned in the introduction and which is characterized in that said first viscoelastic agent contains a concentration of at least one first anaesthetic suitable for use in internal viscoanaesthesia and that said second viscoelastic agent contains a concentration of at least one second anaesthetic suitable for use in external viscoanaesthesia.

The kit of the kind mentioned in the introduction is characterised in that it comprises
  a sterile packaged first hypodermic syringe containing the first viscoelastic agent including at least a first anaesthetic and a hypodermic needle ready for injection, and which is used for internal viscoanaesthesia and
  a second hypodermic syringe containing said second viscoelastic agent as well with a second anaesthetic admixed therein and which is used for external viscoanaesthesia.

By using such a composition set and such a kit it becomes possible to perform an operation with application of a method that may be called viscoanaesthesia. This is achieved by using anaesthetics contained in said first and said second viscoelastic agents which are provided in a ready-to-use condition.

The external viscoanaesthesia is applied only one time about 5 minutes earlier to the start of surgery. Accordingly, the nurse who gives the external viscoanaesthesia may prepare the patient in the waiting time and may announce that the patient is ready for the surgeon. Thus, the surgeon will be ready to work at the patient immediately. Moreover time is saved, seeing that the intraocular anaesthesia is given as part of the steps performed by the surgeon during the surgical intervention.

It may also be possible to introduce other kinds of drugs being of importance for a surgical intervention, preferably cataract surgery. For example, thus antiinflammatorical drugs having a known pain suppressing effect may be introduced. Hereby a possible intensification of pain relief is achieved also after the operation has ended.

By having a composition set and a kit at hand in which the viscoelastic agent, or mixtures of viscoelastica, are combined with the necessary or advantageous anaesthetics to be used in connection with the intervention, it becomes possible to achieve a more efficient operation. Thus the surgeon only has to be in contact with the patient when operation has to be performed, which saves the time previously used in connection with injection anaesthesia and the subsequent waiting time until the operation could be commenced. A considerable rationalisational advantage has appeared by anaesthesia with drops.

Furthermore, it becomes possible to reduce the need for personnel and the risk of variation in the used substances, as the substances may be produced by a standardised mode of production with a consequently reduced risk of mistakes.

Furthermore, a permanent presence of anaesthetic in the eye is ensured with the possibility of a gradual release of the anaesthetic as long as the viscoelastic solution is present in the eye.

By using the composition set according to the invention, it thus becomes possible to perform intraocular anaesthesia simultaneously with introducing the viscoelastic agent which in a traditional way is injected for protecting the inner of the eye and for expanding the eye and for aiding during the lens implantation.

Thus, the addition of local anaesthetics in the viscoelastic agent will cover the need for intraocular anaesthesia by anaesthesia with drops. As the injection is performed at the start of the operation at the same time as the viscoelastic agent has to be injected anyway, a rationalization and simplification is achieved for the benefit of time consumption as well as security. The injection is repeated before the implantation of the lens. By using a viscoelastic agent containing anaesthetics the time for injection and the volume may be maintained.

By using the composition set according to the invention, it thus becomes possible to reduce two procedures into a single procedure with the consequent reduction of risks of contamination and erroneous concentration.

The possibility for spreading the use of intraocular anaesthesia is furthermore increased and thus becomes accessible for more surgeons, as it becomes a direct part of an already used, known procedure in which there is used a viscoelastic agent at surgical intervention.

For the patient the use of the composition set will also be experienced as advantageous as the intervention becomes less unpleasant.

A preferred embodiment for the composition set according to the invention is characterised in that said anaesthetics comprise lidocaine hydrochloride with a concentration between 0.5 and 5%, preferably 1%, that as viscoelastic agents sodium hyaluronate is used, and that sodium hyaluronate is used in concentrations between 5 and 40 mg/ml, preferably between 10 and 20 mg/ml, in Ringer lactate solution or Basic Salt Solution (BSS).

More preferably the composition set is characterised in that said first viscoelastic agent is sodium hyaluroate comprising as anasthethic agent tidocaine hydrochloride in a concentration between 0.5 and 5%, preferably 1%, and that said second viscoelastic agent is sodium hyaluronate comprising as anaesthetic agent lidocaine hydrochloride in a concentration between 2 and 6%, preferably 4%.

In order to reduce the discomfort to the patient, it is preferred that the composition is pH-adjusted and adjusted with respect to osmosis and salt. This takes places preferably with sodium bicarbonate and the pH is adjusted to about 7.

It is preferred to use sodium hyaluronate or sodium chondroitinsulphate as viscoelastics.

The viscoelastic agents may be viscoelastic polymers and may be of the type and have physical properties as disclosed in WO 98/41171, the content of which is hereby incorporated by reference.

An especially appropriate range of shear viscosities for the compositions according to the present invention measured at a shear rate of $39.6s^{-1}$ is 5 to 500 cP, preferably about 200 cP.

It is possible to provide an especially suitable procedure by providing the composition set in the form of a kit which comprises a sterile packaged first hypodermic syringe containing the first viscoelastic agent including at least a first anaesthetic and a hypodermic needle ready for injection, and which is used for internal viscoanaesthesia and a second hypodermic syringe containing said second viscoelastic agent as well with a second anaesthetic admixed therein and which is used for external viscoanaesthesia.

Before an intervention the surgeon may thus provide a kit which after the end of operation may be discarded. In such a kit for use in cataract surgery, the syringe will preferably be arranged for containing between 0.3 and 1.0 ml.

As the kit may contain a first and second syringe each with a viscoelastic agent containing an anaesthetic for use in anaesthesia, it becomes possible to have an anaesthetic kit for the whole surgical intervention.

The second syringe may preferably contain lidocaine hydrochloride in a higher concentration than the first syringe used intraocularily. Preferably said first syringe comprises sodium hyaluronate with lidocaine hydrochloride in a concentration between 0.5 and 5%, preferably 1%, whereas the second syringe comprises sodium hyaluronate with lidocaine hydrochloride in a concentration between 2 and 6%, preferably 4% allowing surface analgesia.

According to a preferred embodiment, the first and the second syringes contain sodium hyaluronate or mixtures of other viscoelastica in concentrations between 5 and 40 mg/ml, preferably between 10 and 20 mg/ml.

The viscoelastic anaesthesian mixture in the second syringe is applied externally in conjunctiva between the lower eyelid and the eyeball approximately 5 minutes before commencing the operation. The patient lies with the eye shut until the operation is commenced. The viscoelastic mixture ensures a good and permanent release of the anaesthestic and the viscoelastic mixture ensures a clear cornea. Also it may be expected that a deeper anaesthesia is achieved by using a viscoelastic agent instead of traditional drops.

The external anaesthesia may possibly be provided at the start of the operation whereby not only the anaesthesia is enhanced, but the cornea is protected against drying out, which implies less need for flushing with liquid during the operation (lubricating effect).

When a kit with two syringes is used, the second syringe is used for an external viscoanaesthesia which is then replacing the anaesthesia with drops.

The first syringe in such a kit is used for an internal viscoanaesthesia instead of the traditional intraocular anaesthesia.

With the composition set and the kit according to the present invention there is thus introduced the above defined new terms in the form of external viscoanaesthesia and internal viscoanaesthesia. By combining the external and internal viscoanaesthesia the operation may thus be performed using the method designated viscoanaesthesia.

In a kit provided according to the invention the two syringes will visually differ from each other so that the user does not mistake the two syringes. The differentiation may be established by size, colour, shape, or in another way.

The syringe intended for external viscoanaesthesia will contain a mixed product with a relatively high concentration of anaesthesia and a relatively low viscosity which is depending on the concentration and kind of viscoelastic agent. Contrary to this, the syringe for internal viscoanaesthesia will contain an agent with a relatively low concentration of anaesthesia and a relatively high viscosity depending on the concentration and kind of viscoelastic agent.

The agent contained in each of the syringes may well be present without any preservation agents so that a risk of toxicity to the cornea is avoided.

By using viscoanaesthesia a simplified operation and an experience of less discomfort on the patient is achieved.

Used as viscoelastics are methyl hydroxypropyl cellulose, sodium hyaluronate, or sodium chondroitinsulphate, or mixtures thereof, or other viscoelastic agents for use in connection with intraocular operations. Concentrations between 5 and 40 mg/ml, preferably between 10 and 20 mg/ml, are used.

A composition set or a kit according to the invention may alternatively be used in connection with other surgical interventions than cataract operations. Alternatively, it may thus be used by other kinds of intraocular operations where a viscoelastic agent is applied.

What is claimed is:

1. A composition set for use in intraocular surgery comprising a first viscoelastic agent which contains a first concentration of at least one first anaesthetic suitable for use in internal viscoanaesthesia and a second viscoelastic agent which contains a second concentration of at least one second anaesthetic suitable for use in external viscoanaesthesia.

2. A composition set according to claim 1, wherein said first and second anaesthetic comprise a local anaesthetic.

3. A composition set according to claim 1, wherein said first and second anaesthetics comprise lidocaine hydrochloride and said first and second viscoelastic agents comprise sodium hyaluronate.

4. A composition set according to claim 1, wherein said first and second anaesthetics comprise lidocaine hydrochloride at a concentration between 0.5 and 5%, and wherein said first and second viscoelastic agent is sodium hyaluronate in concentrations between 5 and 40 mg/ml in Ringer lactate solution.

5. A composition set according to claim 1, wherein said first viscoelastic agent is sodium hyaluronate comprising as anaesthetic agent lidocaine hydrochloride in a concentration between 0.5 and 5%, and wherein said second viscoelastic agent is sodium hyaluronate comprising as anaesthetic agent lidocaine hydrochloride in a concentration between 2 and 6%.

6. A composition set according to claim 1, wherein said first and second agents are pH-adjusted and balanced with respect to osmosis and salt with the purpose of avoiding discomfort when applied to a patient.

7. A kit for use in intraocular surgery comprising a first viscoelastic agent and second viscoelastic agent, comprising a sterile packaged first hypodermic syringe containing the first viscoelastic agent including at least a first anaesthetic and a hypodermic needle ready for injection, and a second hypodermic syringe containing said second viscoelastic agent as well with a second anaesthetic mixed therein and which is used for external viscoanaesthesia.

8. A kit according to claim 7, wherein said first syringe comprises sodium hyaluronate with lidocaine hydrochloride in a concentration between 0.5 and 5%, and wherein the second syringe comprises sodium hyaluronate with lidocaine hydrochloride in a concentration between 2 and 6%.

9. A kit according to claim 7, wherein both the first and the second syringe contain sodium hyaluronate or mixtures of other viscoelastics in concentrations between 5 and 40 mg/ml.

10. A composition set according to claim 4, wherein said first and second anaesthetics comprise lidocaine hydrochloride in a concentration of 1% and sodium hyaluronate in a concentration between 10 and 20 mg/ml.

11. A composition set according to claim 5, wherein said first viscoelastic agent comprises lidocaine hydrochloride in a concentration of 1% and said second viscoelastic agent comprises lidocaine hydrochloride in a concentration of 4%.

12. A kit according to claim 8, wherein said first syringe comprises lidocaine hydrochloride in a concentration of 1% and said second syringe comprises lidocaine hydrochloride in a concentration of 4%.

13. A kit according to claim 9, wherein said concentrations are between 10 and 20 mg/ml.

* * * * *